(12) United States Patent
Martens et al.

(10) Patent No.: US 8,694,105 B2
(45) Date of Patent: Apr. 8, 2014

(54) NEUROSTIMULATION SYSTEM HAVING A CONTROLLER FOR CONTROLLING THE SUPPLY OF ELECTRICAL PULSES

(75) Inventors: Hubert Cecile Francois Martens, Eindhoven (NL); Michel Marcel Jose Decre, Eindhoven (NL); Eugenio Cantatore, Eindhoven (NL)

(73) Assignee: Sapiens Steering Brain Stimulation B.V. (NL)

( * ) Notice: Subject to any disclaimer, the term of this patent is extended or adjusted under 35 U.S.C. 154(b) by 194 days.

(21) Appl. No.: 12/667,399

(22) PCT Filed: Jul. 3, 2008

(86) PCT No.: PCT/IB2008/052673
§ 371 (c)(1),
(2), (4) Date: Dec. 31, 2009

(87) PCT Pub. No.: WO2009/007883
PCT Pub. Date: Jan. 15, 2009

(65) Prior Publication Data
US 2010/0198315 A1    Aug. 5, 2010

(30) Foreign Application Priority Data
Jul. 10, 2007 (EP) .................................... 07112150

(51) Int. Cl.
*A61N 1/36* (2006.01)
(52) U.S. Cl.
USPC .............................................. 607/45; 607/68
(58) Field of Classification Search
USPC ...................................... 600/378; 607/45, 57
See application file for complete search history.

(56) References Cited

U.S. PATENT DOCUMENTS

| | | | |
|---|---|---|---|
| 6,016,449 A * | 1/2000 | Fischell et al. | 607/45 |
| 6,516,227 B1 | 2/2003 | Meadows | |
| 7,006,859 B1 * | 2/2006 | Osorio et al. | 600/378 |
| 7,050,856 B2 | 5/2006 | Stypulkowski | |
| 7,127,298 B1 | 10/2006 | He | |
| 7,917,221 B2 * | 3/2011 | Tass | 607/45 |
| 2003/0083724 A1 | 5/2003 | Jog | |
| 2004/0153129 A1 | 8/2004 | Pless | |
| 2005/0055064 A1 * | 3/2005 | Meadows et al. | 607/45 |

(Continued)

FOREIGN PATENT DOCUMENTS

| | | |
|---|---|---|
| JP | 2001-522274 | 12/2005 |
| WO | 2005039694 A1 | 5/2005 |
| WO | 2006/010837 A2 | 2/2006 |
| WO | 2006044793 A2 | 4/2006 |

OTHER PUBLICATIONS

English Translation of the Office Action for Japanese patent application No. 2010-515633, mailed Jul. 2, 2013.

(Continued)

*Primary Examiner* — Carl H Layno
*Assistant Examiner* — Paula J Stice
(74) *Attorney, Agent, or Firm* — Morgan, Lewis & Bockius LLP

(57) ABSTRACT

The invention relates to a neurostimulation system, particularly for deep brain stimulation (DBS), comprising a spatial array (130) of stimulation electrodes (132) and an associated controller (110). The controller (110) is adapted to sequentially supply electrical pulses to different subsets of the stimulation electrodes (132). Preferably, the controller (110) comprises a single pulse-generator (112) and a multiplexing unit (111) for distributing the pulses to different stimulation electrodes. The stimulation electrodes (132) may preferably be arranged on probes (131).

10 Claims, 4 Drawing Sheets

(56) References Cited

U.S. PATENT DOCUMENTS

| | | |
|---|---|---|
| 2006/0004422 A1 | 1/2006 | De Ridder |
| 2006/0212093 A1 | 9/2006 | Pless |
| 2006/0229687 A1 | 10/2006 | Goetz |
| 2006/0276866 A1* | 12/2006 | McCreery .................... 607/116 |
| 2007/0123758 A1 | 5/2007 | Miesel |
| 2007/0142874 A1* | 6/2007 | John .............................. 607/45 |
| 2008/0046023 A1* | 2/2008 | Fischell ......................... 607/45 |

OTHER PUBLICATIONS

Notification of examination transfer before appeal, dated Dec. 13, 2013, for Japanese Patent Application No. 2010-515633.

* cited by examiner

NEUROSTIMULATION SYSTEM HAVING A CONTROLLER FOR CONTROLLING THE SUPPLY OF ELECTRICAL PULSES

FIELD OF THE INVENTION

The invention relates to a neurostimulation system, particularly a central nervous system stimulation (CNSS) or a deep brain stimulation (DBS) system, comprising a plurality of stimulation electrodes. Moreover, it relates to a method for controlling such a DBS system.

BACKGROUND OF THE INVENTION

Electrical stimulation of brain regions by implanted electrodes is a possible therapy for several neural disorders. The WO 2005/039694 A1 discloses a cerebral electrostimulation device comprising a plurality of biocompatible electrodes with several active areas each, wherein said active areas can selectively be connected by a commutation device to lines carrying stimulation pulses. The connection pattern of the commutation device can be modified if necessary to adjust the location of stimulation during or after a surgical intervention. During the normal operation of the device, the connection pattern is however fixed, and only a subset of all available active areas is provided with electrical pulses.

SUMMARY OF THE INVENTION

Based on this background it is an object of the present invention to provide means for improving the electrophysiological efficiency of a neurostimulation system, particularly a CNSS or a DBS system.

This object is achieved by a neurostimulation system according to claim 1 and a method according to claim 1. Preferred embodiments are disclosed in the dependent claims.

The neurostimulation system according to the present invention is suited for neurostimulation, particularly in the central nervous system (CNS) and most preferably for deep brain stimulation (DBS). It comprises the following characteristic components:

a) A plurality of stimulation electrodes that are arranged in a spatial array. The term "array" shall denote in the context of the present application any arbitrary two- or three-dimensional arrangement of a plurality of units. Often the units of such an array will be arranged in a regular pattern, for example a grid or matrix pattern. In other applications, the units may have no particular or regular spatial relation with respect to each other, as is the case for example for DBS electrodes implanted in two different hemispheres of the brain. The stimulation electrodes serve for electrically stimulating neural tissue during the application of the neurostimulation system and are preferably made from a biocompatible metal. Different electrode shapes are possible, for example electrodes extending in a ring shape around some carrier or so-called directional electrodes whereby each directional electrode spans only a limited angle, thus allowing a more focused delivery of electrical stimuli to the tissue. A typical number of stimulation electrodes ranges from two electrodes to five hundred electrodes.

b) A controller for controlling the sequential supply of electrical pulses to different subsets of all stimulation electrodes. The subsets may optionally comprise just one electrode, or they may comprise several electrodes. Preferably each stimulation electrode will be the member of one and only one subset. Moreover, the term "pulse" is to be understood in a broad sense as an electrical signal of arbitrary shape but with a limited temporal duration. Typically, the pulse will have a shape that rises from zero to a peak and then returns to zero, as is the case for example for rectangular or bell-shaped pulses. Pulses or waveforms having phases of opposite polarity are possible as well, e.g. biphasic pulses.

Furthermore, it should be noted that the controller may optionally be connected by wire, by radio link, optically or in any other mechanical, galvanic or wireless way to the stimulation electrodes.

The neurostimulation system will typically—at least in parts—be implantable and biocompatible, have a sufficient (preferably rechargeable) power supply etc. These requirements are known to a person skilled in the art and therefore not explicitly mentioned in the following.

The proposed neurostimulation system has the advantage to stimulate a large volume of neural tissue by using a spatial array of stimulation electrodes. Moreover, the system allows for a stimulation scenario in which not all available stimulation electrodes are activated simultaneously but in which different subsets of these electrodes are activated one after the other. Verification in simulation models and in practice shows that this approach surprisingly yields a higher efficiency and an increased volume of stimulated neural tissue.

The controllers of neurostimulation systems usually comprise electronic units called "pulse-generators" for generating the electrical pulses that are then supplied to the stimulation electrodes. In the proposed neurostimulation system, one such pulse-generator may in principle be present for every stimulation electrode, allowing to provide each electrode with an individual pulse pattern.

In a preferred embodiment of the neurostimulation system, the controller comprises however at least one pulse-generator for generating electrical pulses and a pulse-distribution device for distributing electrical pulses generated by said pulse-generator across at least some of the subsets of electrodes in a timed fashion. By using a pulse-distribution device, the pulse-generator output can be shared by several stimulation electrodes. This reduces the hardware expense and thus the costs and allows for a more compact design of the neurostimulation system. Moreover, the electrical power that the pulse-generator can provide is completely available for the subset of stimulation electrodes which is selected at the moment. In contrast to this, a simultaneous activation of all stimulation electrodes would leave correspondingly less power for the single electrodes.

A very flexible stimulation can be achieved if it is possible to have different pulse-generators sending different pulse trains with possibly different characteristics to different electrode subsets. This can be realized in a first embodiment by providing a plurality of pulse-generators, wherein each of these pulse-generators is associated with a specific pulse-distribution device. In an alternative embodiment, the neurostimulation device comprises a plurality of pulse-generators, and the (at least one) pulse-distribution device can couple different pulse-generators to different subsets of all stimulation electrodes. Thus a single pulse distribution device may for example have n (number of pulse generators) inputs and m (number of electrodes) outputs, wherein any of the n inputs is independently coupled to any subset of the m outputs.

The pulse-distribution device may be realized in several ways, for example:

(1) As a more or less constant routing of pulse-generators to subsets of stimulation electrodes, whereby the pulse-generators "fire" in sequence.

(2) As a multiplexing unit which dynamically distributes pulses generated by the pulse-generator(s) to different stimulation electrodes such that one and only one subset of electrodes is activated at a time.

(3) As a "channeled" multiplexing unit by which the output of the pulse generator(s) is dynamically multiplexed to a limited number of "channels" (e.g. 4, 8, etc.) and whereby each of these channels is connected to a subset of stimulation electrodes. This solution has the advantage that (as the subsets will typically be fixed or changed only once in a while, e.g. during doctor visit) there needs to be less switching in the multiplexer thereby saving power.

The controller of the neurostimulation system is adapted to sequentially supply electrical pulses to different subsets of all stimulation electrodes. In general, the sequence with which subsets are chosen for receiving a pulse and even the partition of all stimulation electrodes into subsets may continuously change. The stimulation electrodes provided with an electrical pulse might for example be randomly selected from the pool of all stimulation electrodes. In a preferred embodiment, the controller is however adapted to apply electrical pulses cyclically to the (fixed) subsets of stimulation electrodes. This means that the subsets of stimulation electrodes have an order in which they are selected for receiving an electrical pulse and that the selection restarts with the first subset of the order after all subsets have been selected once. If the distributed electrical pulses are generated at a constant frequency F and if N subsets are available for selection, then each single subset of stimulation electrodes will receive pulses with a frequency f=F/N. This guarantees optimal stimulation conditions for the surrounding neural tissue.

The controller of the neurostimulation system may preferably be adapted to supply electrical pulses of different waveform to different stimulation electrodes. Thus each subset of stimulation electrodes could receive its own specific stimulus waveform/pulse. Moreover, different current/voltage levels could be applied to stimulation electrodes within a subset to shape the activation volumes of a given subset.

In a preferred embodiment of the invention, the neurostimulation system comprises a plurality of probes that are arranged in a spatial array and that carry at least one of the stimulation electrodes each. The probes typically have an elongated probe body made from a flexible, physiologically compatible and electrically isolating material, for example from polyimide, or polyurethanes and silicone-urethane copolymers. A typical number of probes ranges from two to ten, with each probe having from one to about fifty stimulation electrodes.

In the following, different variations of the aforementioned neurostimulation system with probes are described.

In principle it is possible that the subsets of simultaneously activated stimulation electrodes comprise electrodes from different probes; the subsets might for example comprise one electrode from each probe. In a preferred embodiment, each subset comprises however stimulation electrodes (or just one stimulation electrode) from one associated probe only. At a given point in time, only the tissue around a particular probe will then be stimulated.

In a preferred embodiment, the probes have an axial extension and are arranged parallel to each other (with respect to said axial extension). The probes can then simultaneously be inserted into the brain tissue by a movement along their axis, and the probes can optionally be mounted on a common carrier.

In another embodiment, the subsets of stimulation electrodes are arranged such that the activation volumes of the subsets touch with no or only little overlap (e.g. less than 10%), wherein the "activation volume" of a set of electrodes is defined as the volume around said electrodes in which neural tissue is significantly affected (e.g. depolarized) by a (typical) electrical pulse routed to the electrodes. As their activation volumes touch, the subsets of stimulation electrodes effectively define a larger, connected volume of brain tissue that can be controlled by the neurostimulation system. In a particular embodiment of this design, all stimulation electrodes of each subset may be located on one associated probe.

In the case of axially extending parallel probes, a diameter of the probes can be defined that is measured perpendicular to their axial extension. In a preferred embodiment of the neurostimulation system, the probes are then arranged at a distance from each other that corresponds to 1-times to 10-times their diameter.

Moreover, the probes are preferably distributed over an area (measured perpendicular to their axial extension) of about 20 mm$^2$ to about 400 mm$^2$.

A preferred spatial arrangement of the probes is a regular pattern, for example a pattern in which the probes are located at corners and optionally also in the middle of a rectangle. Alternatively, a triangular or hexagonal pattern can be used.

The invention further relates to a method for controlling a plurality of stimulation electrodes of a neurostimulation system that are arranged in a spatial array. The method comprises the following steps:

a) Generating a sequence of electrical pulses.

b) Distributing said pulses sequentially to different subsets of stimulation electrodes.

The method comprises in general form the steps that can be executed with a neurostimulation system of the kind described above. Therefore, reference is made to the preceding description for more information on the details, advantages and improvements of that method.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

DETAILED DESCRIPTION OF THE INVENTION

The beneficial therapeutic effects of the application of small electric stimuli to central nervous tissue have been discovered by Benabid and co-workers (Grenoble) in the late 1980s. Applying the so-called high-frequency electrical stimulation (130 Hz, −3 V, 60 µs, typical stimulation parameters) to thalamic structures could relieve both Parkinson's disease (PD) patients and Essential Tremor (ET) patients from their tremor. In later years, other targets for deep brain stimulation (DBS) have been identified (e.g. internal segment of the globus pallidus, GPi, and subthalamic nucleus, STN) that resulted in marked improvements of quality of life of PD patients. Moreover, the use of DBS for other neurological disorders like epilepsy and depression is being examined.

In the following, a neurostimulation system according to the present invention will be described with respect to an application for DBS. It should however be noted that the invention is not limited to this case and that it can be applied in other fields of neurostimulation, too.

Figure 1:
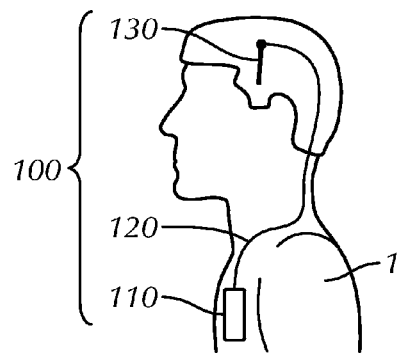
FIG. 1 shows schematically the application of a system according to the present invention for deep brain stimulation.

A typical DBS system 100 is shown in FIG. 1 and consists of:
an implanted controller 110 that is surgically implanted below the clavicle of a patient 1 and supplies the necessary voltage pulses 134b,
an extension wire 120 connected to the controller 110 and running subcutaneously along the neck to the skull where it terminates in a connector, and
the DBS probe arrangement 130 that is implanted in the brain tissue through a burr-hole in the skull.

One possible approach to improve the efficacy of the therapy is to increase the number of electrodes and/or probes (entities carrying electrodes) used for the application of stimulation. By covering a larger volume of tissue more symptoms can be treated more effectively while simultaneously reducing side-effects by not delivering stimulation to unwanted locations.

As model calculations show, the parallel connection of multiple electrodes distributed in a volume of tissue to the output of an implanted pulse-generator does however not result in a proportional increase of stimulation efficacy. Effectively, the stimulated volume per electrode drops in this way. As a consequence if one distributes the pulse-generator output over N electrodes, the increase in stimulated volume of tissue is significantly less than N-fold.

The solution to this problem that is proposed here comprises the connection of the stimulation electrodes in a sequential manner to the pulse-generator output. This is for example achieved by:
1. Driving the pulse-generator at a frequency N·f, where N is the number of electrodes or subsets of (simultaneously addressed) electrodes used to apply stimulation and f is the required therapeutic stimulation frequency.
2. Routing the pulse-generator output to a different electrode or subset of electrodes for each pulse.

Figure 2:
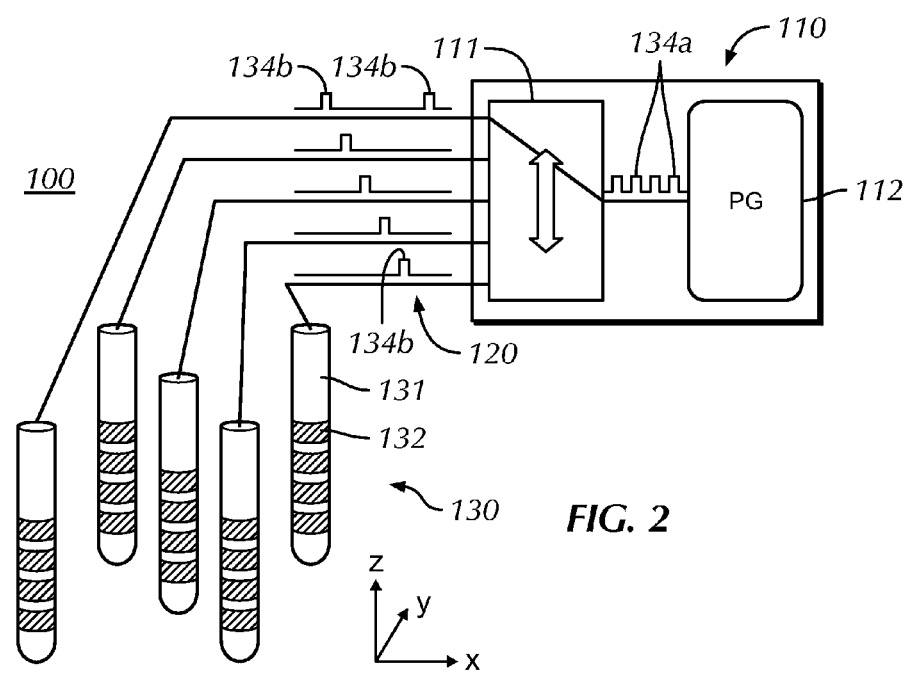
FIG. 2 shows the electrode arrangement of the DBS system of FIG. 1 in more detail.
Figure 3A:
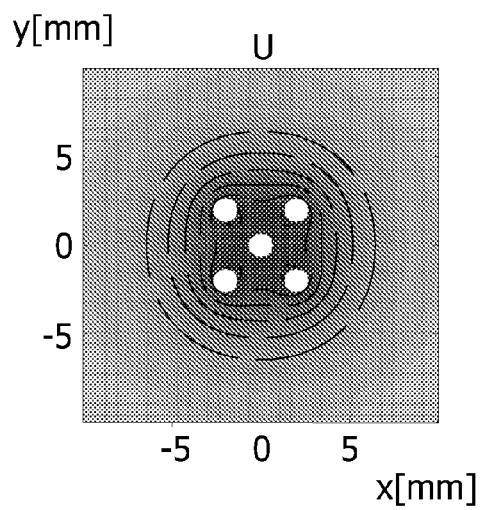
FIGS. 3a-3d show simulation results for the simultaneous activation of all stimulation electrodes in an arrangement like that of FIG. 2.
Figure 3B:
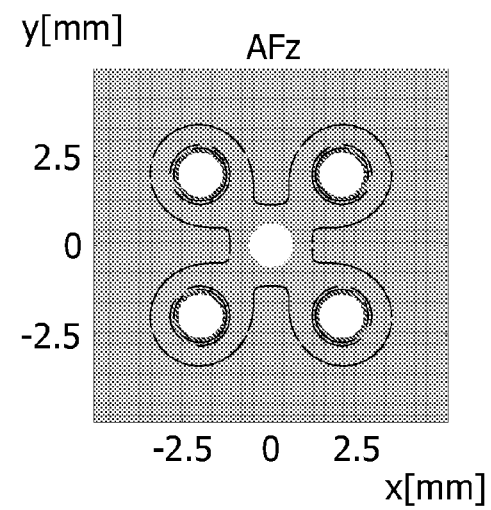
Figure 3C:
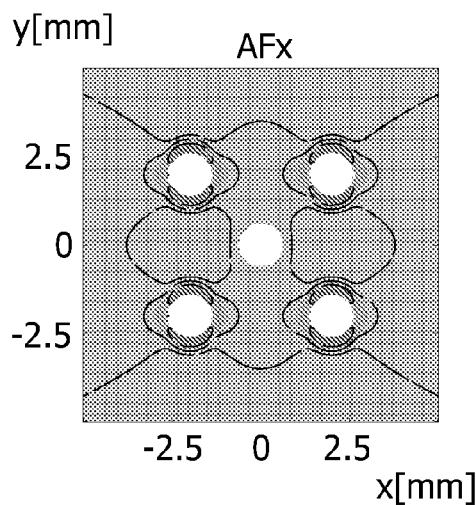
Figure 3D:
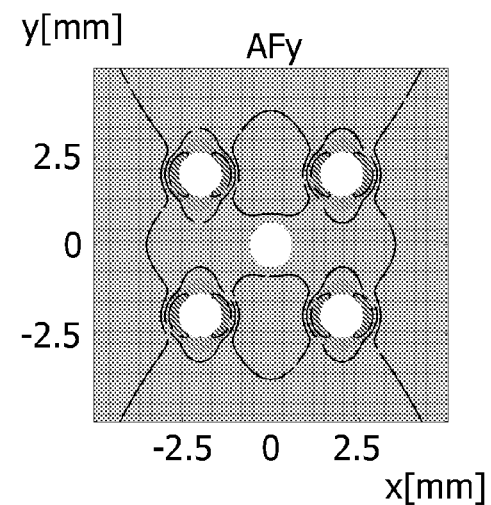
Figure 4A:
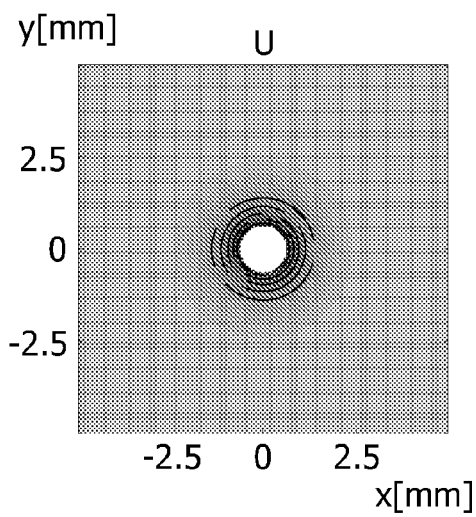
FIGS. 4a-4d show simulation results for the stimulation of a single electrode only.
Figure 4B:
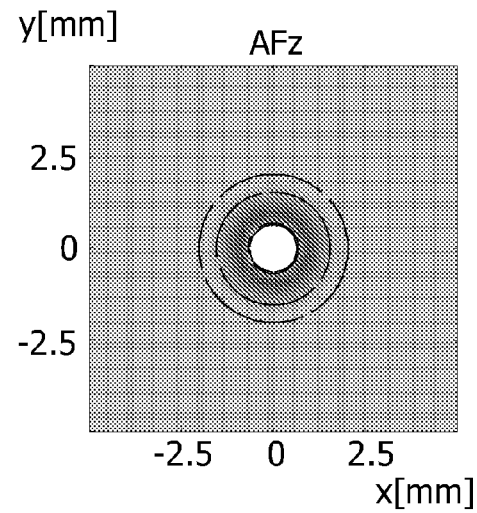
Figure 4C:
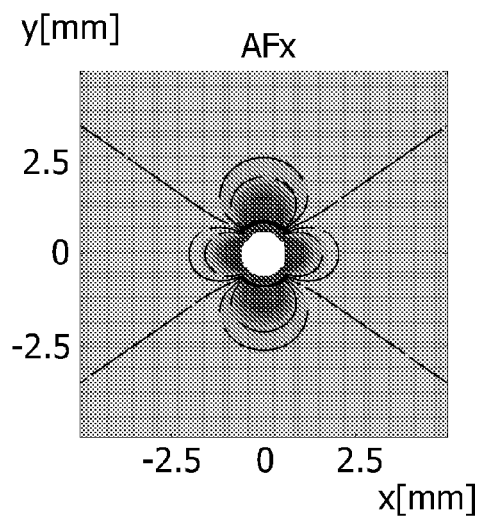
Figure 4D:
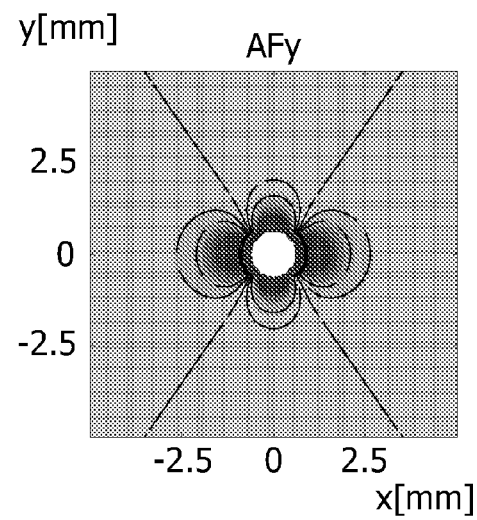

FIG. 2 illustrates this principle for a particular realization of the DBS system 100 of FIG. 1. In the shown case, the DBS system 100 comprises a spatial pattern or array 130 of five probes 131 that extend axially in z-direction and that are arranged parallel to each other in a regular pattern. Each probe 131 carries a plurality of (in the shown example four) ring-shaped stimulation electrodes 132 that are distributed at equal distances from each other along the axial extension of the probes. In the shown example, the five probes 131 are arranged at the corners and in the middle of a square with a side length of typically 8 to 12 mm, and the probes have a typical diameter of about 1.27 mm. The stimulation electrodes 132 have a typical height of about 1.5 mm and are distributed at equal distances of typically about 0.5 mm from each other along the axial extension of the probes.

The stimulation electrodes 132 of the probes 131 are electrically connected by lines 120 to a controller 110 that distributes stimulation pulses 134b over the various stimulation electrodes according to the invention. The controller contains at least one pulse-generator 112 and a multiplexer unit 111. The controller is preferably contained within in a first hermetic biocompatible containment. The multiplexing unit 111 may be physically located within said first containment. However, the multiplexing unit may also be located outside said first containment and integrated in a second hermetic biocompatible containment, for instance a containment on the extension wire connecting to the probes.

The pulse-generator 112 supplies electrical pulses 134a to the input of the multiplexing unit 111. The controller controls the distribution of the electrical pulses 134a over the various electrodes by appropriately switching the multiplex unit. In the shown example, all four stimulation electrodes 132 of a single probe 131 are connected via the same line to the same output of the multiplexing unit 111. The multiplexing unit 111 is connected at its input to the pulse-generator 112 which provides a sequence of rectangular pulses 134a with a frequency Nf (with N=5 here). The multiplexing unit 111 distributes these pulses 134a to its different outputs, i.e. to the different stimulation electrodes 132 of the probe array 130.

Figure 5A:
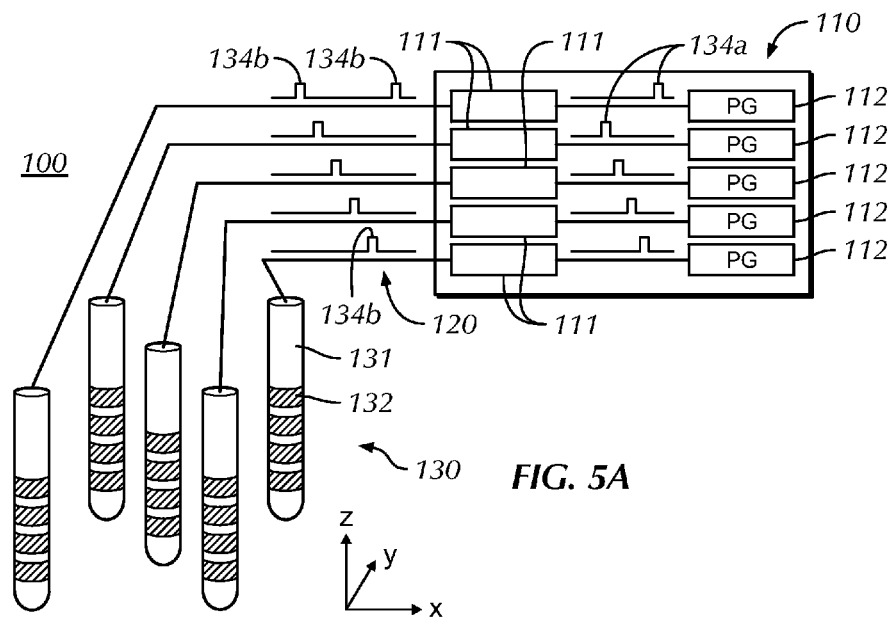
FIGS. 5a and 5b show alternative controller arrangements of the DBS system of FIG. 2.
Figure 5B:
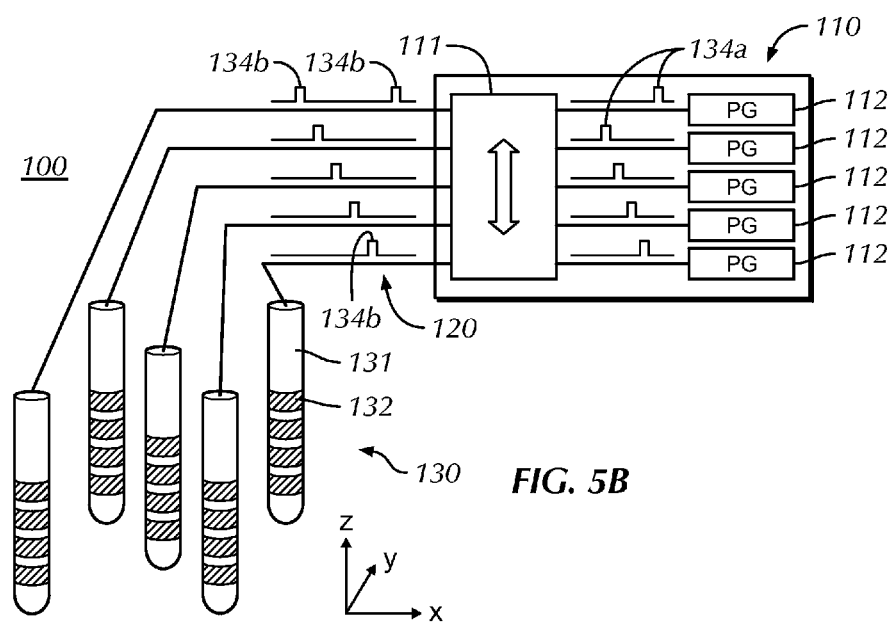

FIG. 5a illustrates a DBS system 100 having a plurality of pulse-generators 112, each having an associated pulse-distribution device 111. FIG. 5b illustrates a DBS system 100 having a plurality of pulse-generators 112 wherein the pulse-distribution device 111 can couple different pulse-generators 112 to different subsets of all stimulation electrodes 132.

Other connection schemes than the shown one may be realized, for example connecting each single stimulation electrode to a separate output and/or connecting stimulation electrodes of several probes to one output. Moreover, it should be noted that FIG. 2 is only meant to represent the functionality and not the actual spatial design of the controller 110. Thus it may for example be possible that the multiplexing unit 111 is actually located close to the probes 131 and connected via a (single) line to the pulse-generator 112 that is implanted a distance away.

The described DBS system 100 results in stimulation volumes per electrode that are similar to the conventional case; N-fold distributed stimulation will thus result in (approximately) N-fold increase of activated tissue volume.

FIGS. 3a-3d and 4a-4d illustrate the advantages of the proposed DBS system with the results of computer simulations. FIG. 3 shows the calculated voltage profile and activating function distributions for a volumetric DBS electrode arrangement like that of FIG. 2, wherein all electrodes are assumed to be simultaneously (!) at −1V. The top left plot a) shows the voltage (U) distribution in a 10×10 mm² axial (xy) plane through the probe array center. The top right plot b) shows the activating function (AF) for fibers running in the vertical direction in a 5×5 mm² axial (xy) plane. The bottom left and bottom right plots c) and d) show the activating functions for horizontal fibers in x and y directions respectively. Drawn lines in the AF plots indicate the boundaries where the AF equals −40 mV, −20 mV, 0 mV, 20 mV, and 40 mV.

The diagrams show that not all tissue in between electrodes is activated and also that the gain in total addressed volume is small.

FIGS. 4a-4d show in a representation corresponding to that of FIGS. 3a-3d show the (conventional) single electrode DBS voltage distribution and activation patterns in an axial plane, wherein the electrode is at −1V amplitude.

From the calculations on the two examples shown in FIGS. 3a-3d and 4a-4d, the following conclusions can be drawn about volumetric DBS for the specific example of 5 parallel probes each carrying 4 circumferential electrodes with simul taneous electrode stimulation compared to single-electrode DBS:
- volumetric DBS draws 5-8 times more current;
- the total volume of activation increases 4-fold;
- the volume of activation per electrode is reduced 5-fold;
- the volume of activation does not match anatomical shapes;
- the central area is barely stimulated;
- the stimulation confines to the edges of the array.

The physical causes underlying the relatively poor performance of the volumetric DBS system can be assumed to be a current drop per electrode, especially at centre electrodes, and a reduction of field gradients, again especially at the centre of the array.

All these disadvantages are avoided if the stimulation pattern proposed above is applied, i.e. sending a pulse to only one electrode/probe at a time or to subsets of electrodes, wherein the activation volumes of the different subsets (which are activated sequentially) have optimal overlap (which may for example correspond to a minimal effective overlap).

Finally, it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A method for controlling a plurality of stimulation electrodes of a neurostimulation system that are arranged in an array, the method comprising:
   a) implanting the plurality of stimulation electrodes into brain tissue;
   b) generating a sequence of electrical pulses using at least one pulse generator; and
   c) sequentially distributing each pulse of the sequence of electrical pulses one at a time to different subsets of stimulation electrodes,
   wherein each subset of stimulation electrodes includes a plurality of the plurality of stimulation electrodes.

2. The method according to claim 1, wherein a frequency in which a subset receives a pulse is equal to a frequency the electrical pulses are generated divided by the number of subsets.

3. The method according to claim 1, wherein the frequencies in which the subsets receive the sequence of electrical pulses are out of phase with one another.

4. The method according to claim 1 further comprising:
   implanting the plurality of stimulation electrodes into brain tissue.

5. The method according to claim 1, wherein the pulses are distributed sequentially to different subsets of stimulation electrodes using a multiplexing unit.

6. The method according to claim 1, wherein an activation volume of each subset of the stimulation electrodes at least partially overlaps at least one other activation volume of another subset of the stimulation electrodes.

7. The method according to claim 1, wherein the stimulation electrodes include a plurality of probes, each probe including a subset of stimulation electrodes.

8. The method according to claim 1, wherein the sequence of electrical pulses are generated by a single pulse generator.

9. The method according to claim 1, wherein the distribution of each pulse from the sequence of electrical pulses is configured to yield an increased volume of stimulated neural tissue.

10. A method for controlling a plurality of stimulation electrodes of a neurostimulation system that are arranged in an array, the stimulation electrodes including a plurality of probes, each probe including a subset of stimulation electrodes, the method comprising:
   implanting the plurality of probes into brain tissue;
   generating a sequence of electrical pulses using an implantable pulse generator; and
   sequentially distributing each pulse of the sequence of electrical pulses one at a time to different subsets of stimulation electrodes using a multiplexing unit,
   wherein each subset of stimulation electrodes includes a plurality of the plurality of stimulation electrodes.

* * * * *